United States Patent [19]

Tachibana et al.

[11] Patent Number: 5,664,001
[45] Date of Patent: Sep. 2, 1997

[54] MEDICAL X-RAY IMAGING APPARATUS

[75] Inventors: Akifumi Tachibana; Keisuke Mori; Masakazu Suzuki; Kazunari Matoba, all of Kyoto; Hitoshi Asai, Hamamatsu; Toshitaka Takeguchi, Ogasa-gun; Kazuhisa Miyaguchi, Hamamatsu, all of Japan

[73] Assignees: J. Morita Manufacturing Corporation, Kyoto; Hamamatsu Photonics Kabushiki Kaisha, Shizuoka, both of Japan

[21] Appl. No.: 621,015

[22] Filed: Mar. 22, 1996

[30] Foreign Application Priority Data

Mar. 24, 1995 [JP] Japan ............... 7-066601

[51] Int. Cl.$^6$ .............................................. A61B 6/14
[52] U.S. Cl. .................. 378/98.8; 378/108; 378/146
[58] Field of Search .................. 378/98.8, 108, 378/96, 97, 110, 112, 145, 146, 38, 39, 40

[56] References Cited

U.S. PATENT DOCUMENTS

| 4,433,430 | 2/1984 | Fredzell | 378/108 |
| 4,803,714 | 2/1989 | Vlasbloem | 378/108 X |
| 4,953,189 | 8/1990 | Wang | 378/108 |
| 5,008,915 | 4/1991 | Vlasbloem | 378/108 |
| 5,444,756 | 8/1995 | Pai et al. | 378/108 X |

FOREIGN PATENT DOCUMENTS

| 60-59700 | 4/1985 | Japan | H05G 1/44 |
| 60-160947 | 8/1985 | Japan | A61B 6/14 |
| 61-22841 | 1/1986 | Japan | A61B 6/00 |
| 62-43990 | 2/1987 | Japan | N04N 7/181 |
| 4-48169 | 11/1992 | Japan | A61B 6/14 |
| 6-38950 | 2/1994 | Japan | A61B 6/00 |

*Primary Examiner*—David P. Porta
*Attorney, Agent, or Firm*—Koda and Androlia

[57] ABSTRACT

A medical X-ray imaging apparatus is provided, which comprises an X-ray source, an X-ray imaging device for detecting an image of X-rays having passed through a subject and a swivel member for rotating the X-ray source and the X-ray imaging device around the subject. The X-ray imaging device comprises a CCD sensor for performing the TDI operation and a dosage sensor for detecting X-rays having passed. Dosage signal Y and transfer speed signal X corresponding to the frequency of a false vertical transfer clock are supplied to a divider, and control signal Z is outputted. When control signal Z is supplied to an X-ray control circuit via a delay circuit, the X-ray irradiation dosage of the X-ray source can be feedback-controlled properly.

6 Claims, 8 Drawing Sheets

MEDICAL X-RAY IMAGING APPARATUS

BACKGROUND OF THE INVENTION

1. Field of the Invention

The present invention relates to a medical X-ray imaging apparatus for performing tomographic imaging along a desired tomographic plane of a subject, such as the head, body, and hands and legs of the human body.

2. Description of the Related Art

As related arts, Japanese Unexamined Patent Publication JP-A 61-22841 (1987) and Japanese Unexamined Utility Model Publication JP-U 4-48169 (1992) disclose an X-ray imaging apparatus for performing TDI (Time Delay Integration) of an image signal by changing the frequency of a charge transfer clock in accordance with the movement of an X-ray image formed on a CCD sensor while being moved.

However, in the prior art of JP-A 61-22841 and JP-U 4-48169, in case the CCD sensor causes variations in characteristics or the intensity of X-rays changes, artificial images are generated in an X-ray image, causing not only reduction in image quality and resolution but also the danger of wrong diagnosis. In addition, in the case of dental panoramic imaging, where the X-ray transmission ratio of a subject changes significantly during imaging because of the presence of the vertebra or prosthesis, the signal level of an X-ray image is changed greatly, thereby making the observation very difficult.

Japanese Unexamined Patent Publication JP-A 62-43990 (1988) discloses a method and an apparatus for X-ray imaging by scanning a charge pattern corresponding to X-ray intensity distribution in a space by using an electrometer after X-ray imaging, wherein artifacts (artificial images) are reduced by correcting the X-ray image.

However, in JP-A 62-43990, signal processing completely different from that of the TDI method is performed by using a special X-ray imaging device referred to as an X-ray converting photoconductor made of selenium. It is, therefore, difficult to directly apply the image correction method to the TDI method.

Furthermore, Japanese Unexamined Patent Publication JP-A 60-160947 (1985) discloses a panoramic X-ray imaging apparatus using an X-ray film, wherein autoexposure and central density correction are attained by controlling the tube voltage and tube current of an X-ray generator on the basis of a comparison between X-ray film feeding speed and a residual X-ray dosage having passed through a subject.

Furthermore, Japanese Unexamined Patent Publication JP-A 60-59700 (1985) discloses a panoramic X-ray imaging apparatus which detects a residual X-ray dosage having passed through a subject by using a sensor composed of a plurality of segments and feeds back the detection results to control an X-ray source, wherein autoexposure is compensated for so as to obtain a proper density at the time of starting imaging of a special site.

However, JP-A 60-160947 and JP-A 60-59700 relate to methods of auto exposure and central density correction in a panoramic X-ray imaging apparatus using an X-ray film. It is, therefore, very difficult to directly apply the methods to the TDI method.

Furthermore, Japanese Unexamined Patent Application JP-A 6-38950 (1994) discloses an X-ray imaging apparatus wherein a photodiode for monitoring X-ray dosages is formed on the bottom surface of a substrate so as to control the output of an X-ray source by real-time detection of X-rays having passed through a subject during imaging.

However, since the apparatus described in JP-A 6-38950 performs real-time detection of X-rays having passed through a subject during imaging by using the photodiode disposed on the bottom side, the response of the entire loop must be considerably quick to stabilize an X-ray dosage by feeding back the detection signal to the X-ray source. This cannot be attained easily in actual practice.

SUMMARY OF THE INVENTION

The object of the present invention is to provide a medical X-ray imaging apparatus capable of securely performing autoexposure and density correction and capable of obtaining an easy-to-diagnose X-ray image even when the X-ray transmission ratio of a subject changes during X-ray tomographic imaging using the TDI method.

The invention provides a medical X-ray imaging apparatus comprising:

an X-ray generator for emitting X-rays toward a subject;

an X-ray imaging device for detecting an image of X-rays having passed through the subject;

a swivel member for rotating the X-ray generator and the X-ray imaging device that are opposed to each other around the subject; and display means for displaying an image signal from the X-ray imaging device;

wherein the X-ray imaging device includes a CCD sensor having a plurality of light-receiving pixels arranged in two dimensions and the frequency of a charge transfer clock is changed depending on the rotation speed of the swivel member to perform imaging of a predetermined tomographic plane, characterized in that the X-ray imaging device further includes a dosage sensor for detecting an X-ray dosage having passed the subject, and that the dosage sensor is provided adjacent to the CCD sensor forward in the rotation direction of the CCD sensor to perform feedback-control of the X-ray dosage emitted by the X-ray generator.

In accordance with the invention, since the dosage sensor is provided adjacent to the CCD sensor forward in the rotation direction of the CCD sensor, an X-ray dosage entering the CCD sensor can be detected beforehand. Therefore, a sufficient time can be obtained from X-ray dosage detection to X-ray imaging, and the X-ray dosage from the X-ray generator can be feedback-controlled securely. When the swivel member rotates and an X-ray beam crosses the vertebra during tomographic imaging, for example, the dosage sensor detects a decrease in the X-ray dosage having passed the subject in advance and controls the X-ray generator to increase the X-ray dosage as soon as the same irradiated site reaches the CCD sensor. After the swivel member rotates further and the X-ray beam has finished crossing the vertebra, the X-ray dosage passing through the subject begins to increase again. The X-ray dosage is decreased by controlling the X-ray generator as soon as the same irradiated site reaches the CCD sensor Just as described above. In this way, the change in the X-ray transmission ratio of the subject is detected before the actual imaging operation. The X-ray dosage can thus be controlled properly and an X-ray image having small signal level variations as a whole can be obtained.

Furthermore, in the invention, the dosage sensor has a single or plural light-receiving surfaces.

Furthermore, since the dosage sensor has a single or plural light-receiving surfaces, the advance detection of the X-ray dosage having passed the subject can be attained by using a simple structure. In addition, by obtaining the simple mean value and the weighted mean value of outputs from a plurality of light-receiving surfaces, stabilized X-ray dosage detection can be attained regardless of local changes in the transmission ratio of the subject.

Furthermore, the structure of the dosage sensor can be the same as that of the CCD sensor.

Furthermore, since the structure of the X-ray dosage sensor is the same as that of the CCD sensor, the TDI operation wherein the image of a predetermined tomographic plane is taken by changing the frequency of the charge transfer clock depending on the rotation speed of the swivel member is made possible, and imaging can be performed in advance in the same conditions as those of the CCD sensor. As a result, the situations of the subject can be detected more accurately and the X-ray dosage can be controlled more appropriately.

Furthermore, in the invention, the X-ray dosage from the X-ray generator can be feedback-controlled on the basis of the ratio between the output from the dosage sensor and the frequency of the charge transfer clock.

Furthermore, by feedback-controlling the X-ray dosage on the basis of the ratio between the output from the dosage sensor and the frequency of the charge transfer clock, the X-ray dosage per light-receiving pixel can be controlled properly. When the frequency of the charge transfer clock decreases for example, an X-ray exposure per light-receiving pixel increases. Conversely, when the frequency of the charge transfer clock increases, the X-ray exposure per light-receiving pixel decreases. Accurate exposure control can thus be attained by adjusting the amount of feed back depending on the change in the clock frequency.

Furthermore, in the invention, the dosage sensor comprises a CCD sensor disposed adjacent to the above-mentioned CCD sensor and configured so as to be able to transfer charges In the direction opposite to the CCD sensor.

Furthermore, since the dosage sensor comprising a CCD sensor is disposed adjacent to the imaging CCD sensor, the apparatus can be made compact and produced easily.

Furthermore, in the invention, the dosage sensor comprises a nondestructive signal detector composed of a floating gate amplifier disposed at an array of CCD pixels provided adjacent to the above-mentioned CCD sensor.

BRIEF DESCRIPTION OF THE DRAWINGS

Other and further objects, features, and advantages of the invention will be more explicit from the following detailed description taken with reference to the drawings wherein.

DETAILED DESCRIPTION OF THE PREFERRED EMBODIMENTS

Figure 1:
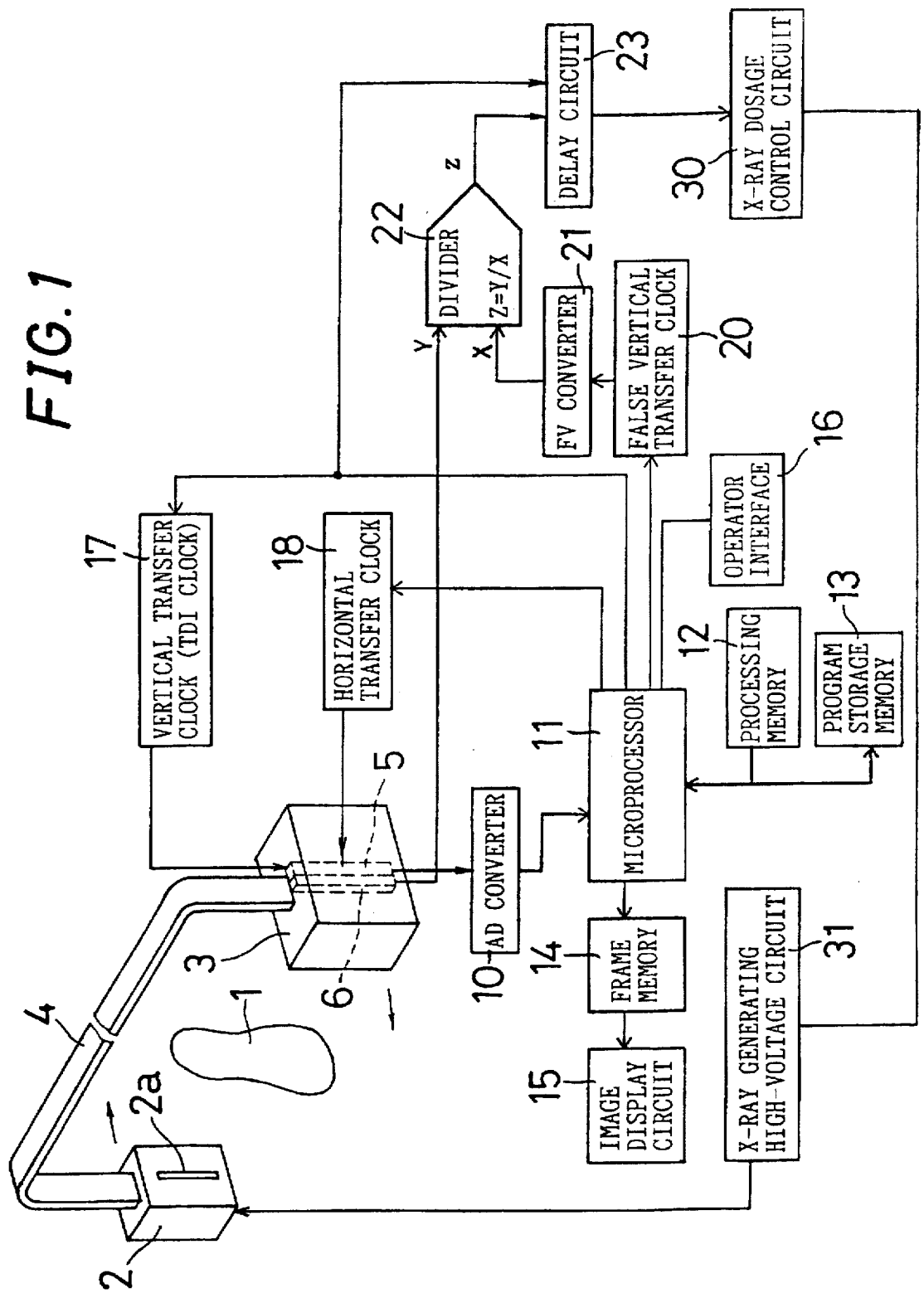
FIG. 1 is a view showing the construction of a first embodiment of the invention.

Now referring to the drawings, preferred embodiments of the invention are described below.

FIG. 1 is a view showing the construction of a first embodiment of the invention. The medical X-ray imaging apparatus in accordance with the first embodiment comprises an X-ray source 2 for emitting X-rays having a vertically long slit shape toward a subject 1, such as the human body, an X-ray imaging device 3 for detecting an image of X-rays having passed through the subject 1 and a swivel member (such as a rotary arm) for holding the X-ray source 2 and the X-ray imaging device 3 opposed to each other and for rotating the X-ray source 2 and the X-ray imaging device 3 around the subject 1. An X-ray tube (not shown) is provided in the X-ray source 2. The X-ray irradiation dosage to the subject 1 is controlled by adjusting imaging conditions, such as tube voltage, tube current and conducting period. The X-rays generated by the X-ray tube are converted into an X-ray beam having a vertically long slit shape as the X-rays pass through a primary slit 2a.

The X-ray imaging device 3 is provided with a secondary slit (not shown) for allowing the X-rays from the X-ray source 2 to pass through. Furthermore, the X-ray imaging device 3 is provided with a scintillator for converting an incoming X-ray image into a visible light image, a fiber optic plate (FOP) for guiding the visible light image from the scintillator and a CCD (charge-coupled device) sensor 5 for taking the visible light image from the fiber optic plate. The CCD sensor 5 has a plurality of light-receiving pixels arranged in two dimensions and performs the TDI (time delay integration) operation, wherein the frequency of the charge transfer clock is changed depending on the rotation speed of the swivel member 4 so as to take an image of a predetermined tomographic face.

The swivel member 4 is supported so as to be rotatable in a horizontal plane around a position just above the subject 1. The rotation shaft of the swivel member 4 is driven by an arm motor, such as a stepping motor, and provided with an angle detector for detecting a change in rotation angle with time. The output of the angle detector is used to synchronize the TDI operation with the charge transfer clock.

The X-ray imaging device 3 is provided with a dosage sensor 6 for detecting an X-ray dosage having passed the subject 1. The dosage sensor 6 is provided adjacent to the CCD sensor 5 forward in the rotation direction of the CCD sensor 5 so as to detect the X-ray dosage to be imaged at the CCD sensor 5 in advance. A semiconductor detector having sensitivity for X-rays, a combination of a scintillator and a photosensor, an X-ray ionization box or the like can be used as the dosage sensor 6. Although the dosage sensor 6 having a single light-receiving surface is used in the present embodiment, a plurality of dosage sensors can also be used.

The back surface of the CCD sensor 5 and the interior of the X-ray imaging device 3 are shielded against X-rays with lead or the like to prevent the adverse effect of scattered X-rays.

The image signal outputted from the CCD sensor 5 is converted into 8-bit (=256 levels) digital data, for example, by an AD converter 10 and supplied to a microprocessor 11 and then stored in a frame memory 14. The image data stored in the frame memory 14 is subjected to a predetermined imaging processing, and indicated by an image display circuit 15, such as a CRT (cathode ray tube), so as to be available for a variety of medical diagnostic purposes. In addition, a processing memory 12 required for signal processing, a program storage memory 13 and an operator interface 16, such as a keyboard and panel switches, are connected to the microprocessor 11.

The microprocessor 11 outputs a vertical transfer clock signal 17 so that the charges received and stored by the CCD sensor 5 can be transferred in the rotation direction of the swivel member 4. The microprocessor 11 also outputs a horizontal transfer clock 18 so that a single scanning line of charges vertically transferred can be read.

On the other hand, an analog signal proportional to the dosage having passed through the subject 1 is outputted from the dosage sensor 6 provided adjacent to the CCD sensor 5 and supplied to a divider 22 as dosage signal Y. A false vertical transfer clock 20 being synchronous with the vertical transfer clock 17 is outputted from the microprocessor 11, converted into an analog signal proportional to the frequency of the clock by an FV converter (frequency-voltage conversion) 21, and supplied to the divider 22 as transfer speed signal X. The divider 22 divides dosage signal Y by transfer speed signal X and outputs control signal Z. As a result, control signal Z increases proportionally as the dosage detected by the dosage sensor 6 increases; control signal Z decreases inversely proportionally as the frequency of the vertical transfer clock 17 increases.

Control signal Z from the divider 22 is delayed once for a predetermined period by a delay circuit 23 and supplied to an X-ray dosage control circuit 30. The delay circuit 23 is provided in consideration of a time delay corresponding to the distance between the dosage sensor 6 and the CCD sensor 5. Accordingly, the delay circuit 23 comprises analog delay lines or the like, the number of which corresponds to the distance between the two sensors plus half of the width of the CCD sensor 5. The vertical transfer clock 17 is used as a driving clock.

In accordance with the delayed control signal Z, the X-ray dosage control circuit 30 controls an X-ray generating high-voltage circuit 31 and feedback-controls the X-ray tube of the X-ray source 2 to adjust imaging conditions, such as tube voltage, tube current, conducting period, etc. In this kind of an X-ray feedback loop, when control signal Z increases, X-ray dosage decreases. Conversely, when control signal Z decreases, negative feedback is performed to increase X-ray dosage. The X-ray dosage per unit time can be measured accurately by considering the change in the frequency of the vertical transfer clock 17 by using the divider 22.

Figure 2:
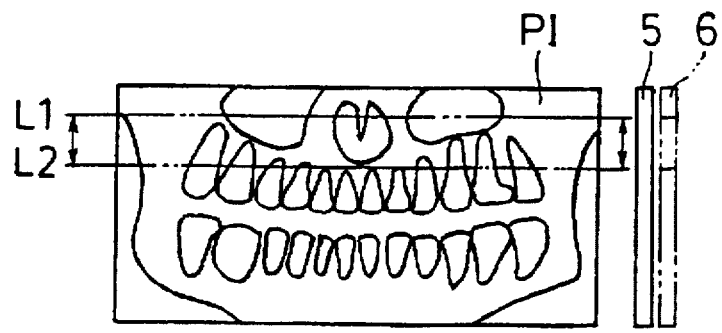
FIG. 2 is an explanatory view showing the arrangement of a dosage sensor 6.

FIG. 2 is an explanatory view showing the arrangement of the dosage sensor 6. The imaging region of the CCD sensor 5 is about 6 mm in width and 150 mm in length, for example. Tomographic image PI can be obtained by rotating the CCD sensor 5 around the subject 1. The light-receiving region of the dosage sensor 6 may be the same as that of the CCD sensor 5, or the dosage sensor 6 may be provided so as to receive light only at a specific region. In the case of digital panoramic imaging, for example, a proper exposure can be attained for the entire image by setting the area between line L1, wherein X-rays passes through the vicinity of the bottom portion of the maxillary sinus, and line L2, wherein X-rays passes through the vicinity of the bottom portion of the upper dental roots, as a sensing region. The dosage sensor may be arranged either front in the direction of rotation of the CCD sensor 5, or in the rear of a gap of a secondary slit (not known), or may be arranged within the secondary slit.

Figure 3:
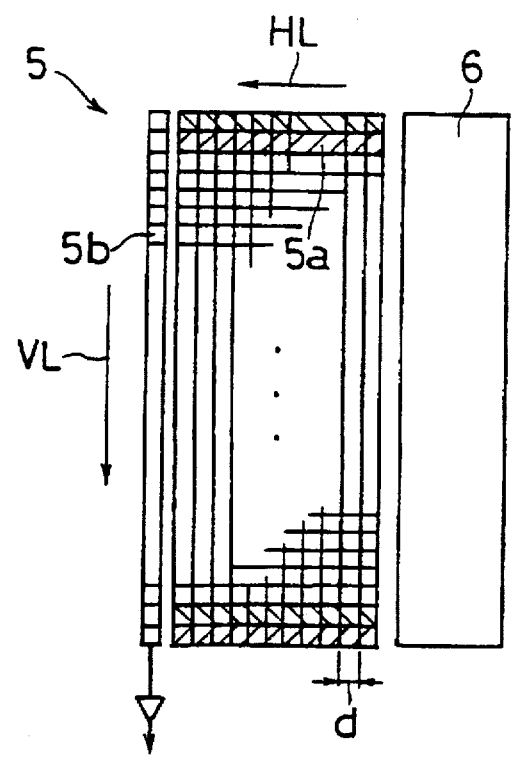
FIG. 3 is a view showing the arrangement of the pixel arrays and charge transfer operation of a CCD sensor 5.

FIG. 3 is a view showing the arrangement of the pixel arrays and charge transfer operation of the CCD sensor 5. In the CCD sensor 5, a vertically long light-receiving portion is formed by a plurality of light-receiving pixels arranged in a two-dimensional matrix. Each light-receiving pixel is electrically connected to a plurality of vertical shift registers 5a (shaded by slant lines in FIG. 3) arranged in horizontal direction HL. The charge on each vertical shift register 5a is transferred sequentially in horizontal direction HL by the vertical transfer clock. The output portion of each vertical shift register 5a is electrically connected to the horizontal shift register 5b arranged in vertical direction VL. Each time the vertical shift register 5a completes the transfer of a charge for one pixel, all the charges are transferred outward. In this way, the X-ray image is converted into a time series electrical signal by the combination of horizontal scanning and vertical scanning. Although the CCD sensor 5 shown in FIG. 3 is a full-frame transfer (FFT) type with no charge storage portion, a frame transfer (FT) type with charge storage portions as many as the light-receiving pixels may also be applicable.

Next, the TDI operation of the CCD sensor 5 is described below. When the swivel member 4 rotates, the X-ray image is moved in the horizontal direction. The speed of the movement varies depending on the position of an X-ray tomographic plane. To solve this problem, the charge transfer speed of the vertical shift register 5a, that is, the frequency of the vertical transfer clock is changed so as to coincide with the movement speed of the X-ray image corresponding to the predetermined tomographic plane. As a result, only the charges due to a desired X-ray tomographic image can be transferred and accumulated (integrated) sequentially. Consequently, only the X-ray image corresponding to a specific charge transfer speed can be taken as a still image, and X-ray images not corresponding to the transfer speed flow away. A tomographic image similar to that obtained by a conventional tomographic imaging apparatus using a film can thus be obtained. A relational equation of $f=v/d$ is established when the frequency of the charge transfer clock signal is f, the film feeding speed of the conventional tomographic imaging apparatus using a film is v, and the distance between the pixels of the CCD sensor 5 is d.

(Second Embodiment)

Figure 4:
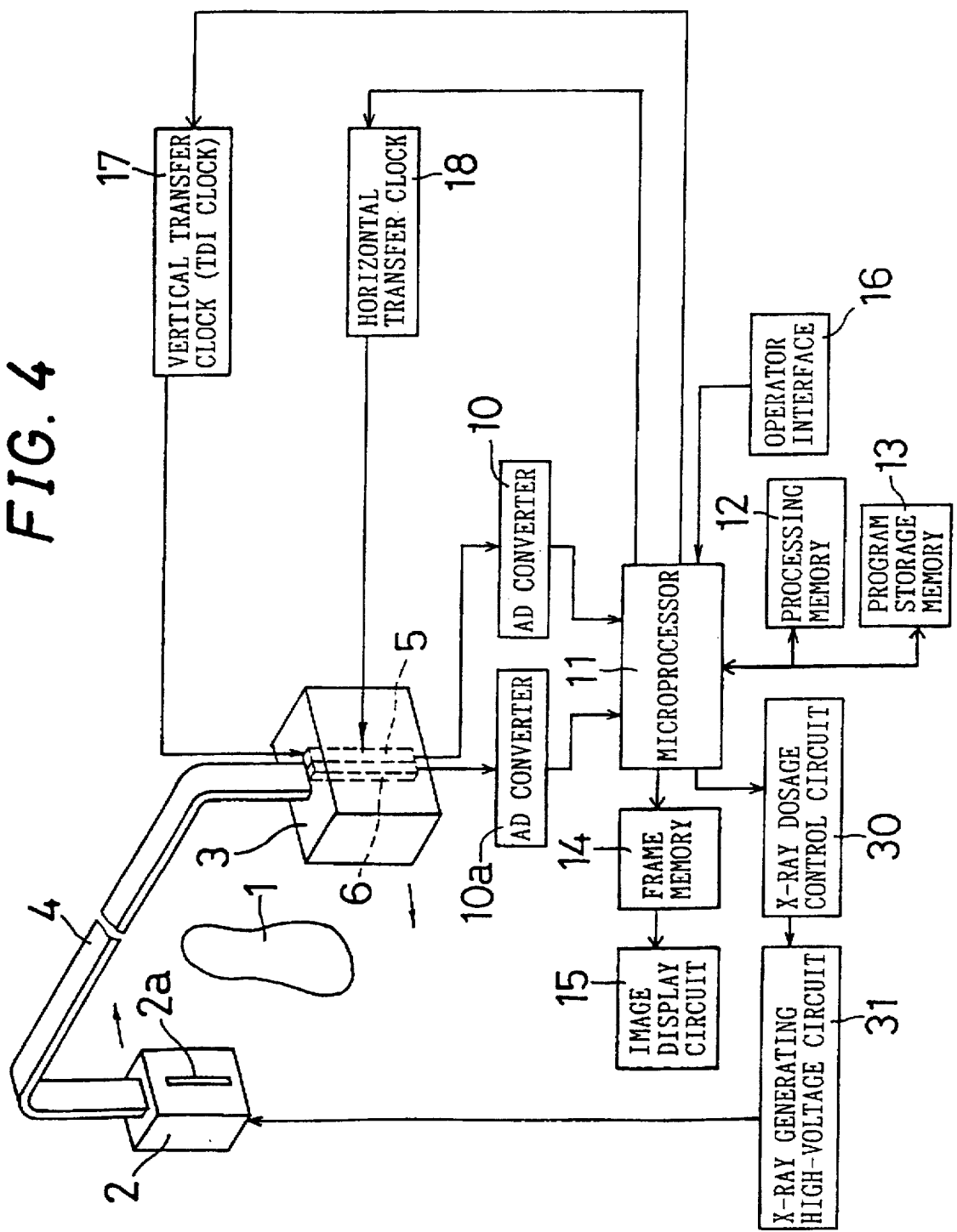
FIG. 4 is a view showing the construction of a second embodiment of the invention.

FIG. 4 is a view showing the construction of a second embodiment of the invention. The medical X-ray imaging apparatus in accordance with the second embodiment comprises an X-ray source 2 for emitting X-rays having a vertically long slit shape toward a subject 1, such as the human body, an X-ray imaging device 3 for detecting an image of X-rays having passed through the subject 1 and a swivel member (such as rotary arm) for holding the X-ray source 2 and the X-ray imaging device 3 opposed to each other and for rotating the X-ray source 2 and the X-ray imaging device 3 around the subject 1. An X-ray tube (not shown) is provided in the X-ray source 2. The X-ray irradiation dosage to the subject 1 is controlled by adjusting imaging conditions, such as tube voltage, tube current and conducting period. The X-rays generated by the X-ray tube are converted into an X-ray beam having a vertically long slit shape as the X-rays pass through a primary slit 2a.

The X-ray imaging device 3 is provided with a secondary slit (not shown) for allowing the X-rays from the X-ray source 2 to pass through. Furthermore, the X-ray imaging device 3 is provided with a scintillator for converting an incoming X-ray image into a visible light image, a fiber optic plate (FOP) for guiding the visible light image from the scintillator and a CCD (charge-coupled device) sensor 5 for taking the visible light image from the fiber optic plate. The CCD sensor 5 has a plurality of light-receiving pixels arranged in two dimensions and performs the TDI (time delay integration) operation, wherein the frequency of the charge transfer clock is changed depending on the rotation speed of the swivel member 4 so as to take an image of a predetermined tomographic face.

The swivel member 4 is supported so as to be rotatable in a horizontal plane around a position just above the subject 1. The rotation shaft of the swivel member 4 is driven by an arm motor, such as a stepping motor, and provided with an angle detector for detecting a change in rotation angle with time. The output of the angle detector is used to synchronize the TDI operation with the charge transfer clock.

The X-ray imaging device 3 is provided with a dosage sensor 6 for detecting an X-ray dosage having passed the subject 1. The dosage sensor 6 is provided adjacent to the CCD sensor 5 forward in the rotation direction of the CCD sensor 5 so as to detect the X-ray dosage in advance to be imaged at the CCD sensor 5. A semiconductor detector having sensitivity for X-rays, a combination of a scintillator and a photosensor, an X-ray ionization box or the like can be used as the dosage sensor 6. In this embodiment, the dosage sensor 6 having a plurality of light-receiving surfaces arranged in one dimension is used and configured so that a dosage detection region such as that shown in FIG. 2 can be set as desired.

The image signal outputted from the CCD sensor 5 is converted into 8-bit (=256 levels) digital data, for example, by an AD converter 10 and supplied to a microprocessor 11 and then stored in a frame memory 14. The image data stored in the frame memory 14 is subjected to a predetermined imaging processing, and indicated by an image display circuit 15, such as a CRT (cathode ray tube), so as to be used for a variety of medical diagnostic purposes. In addition, a processing memory 12 required for signal processing, a program storage memory 13 and an operator interface 16, such as a keyboard and panel switches, are connected to the microprocessor 11.

The microprocessor 11 outputs a vertical transfer clock 17 so that the charges received and stored by the CCD sensor 5 can be transferred in the rotation direction of the swivel member 4. The microprocessor 11 also outputs a horizontal transfer clock 18 so that a single scanning line of charges vertically transferred can be read.

On the other hand, an analog signal proportional to the dosage having passed through the subject 1 is outputted from the dosage sensor 6 provided adjacent to the CCD sensor 5. The signal is converted into 8-bit (=256 levels) digital data, for example, by an AD converter 10a, supplied to a microprocessor 11 and stored in a processing memory 12 so as to be used for feedback control of X-rays generated from the X-ray source 2.

In accordance with instructions from the microprocessor 11, an X-ray dosage control circuit 30 controls an X-ray generating high-voltage circuit 31 and feedback-controls the X-ray tube of the X-ray source 2 to adjust imaging conditions, such as tube voltage, tube current, conducting period, etc.

Figure 5:
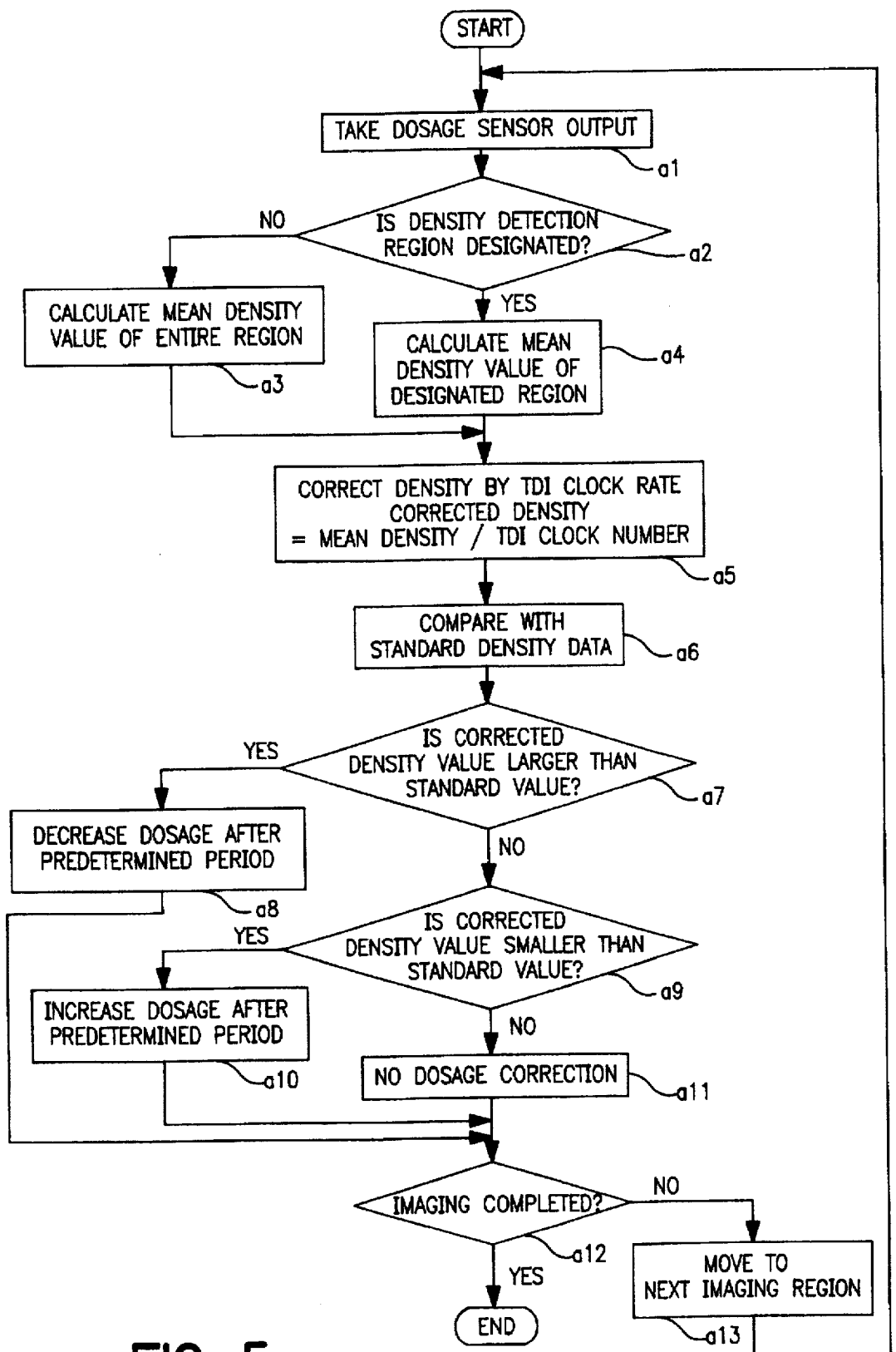
FIG. 5 is a flowchart showing the operation of the second embodiment.

FIG. 5 is a flowchart showing the operation of the second embodiment. When tomographic imaging starts, the output from the dosage sensor 6 is supplied to the microprocessor 11 in step a1. Next, whether a density detection region has been designated or not is determined in step a2. When no region has been designated, the mean value of the density in all the regions is calculated in step a3. On the other hand, when an region has been designated, the mean value of the density in the designated region is calculated in step a4.

Next, in step a5, data correction is performed in accordance with the TDI clock rate. A corrected density value is obtained by dividing the mean value of the density calculated in step a3 or a4 by the number of TDI clock pulses per unit time. This correction process corresponds to the process conducted by the divider 22 shown in FIG. 1. The X-ray dosage per unit time can be measured accurately by considering the change in the frequency of the vertical transfer clock 17.

Next, the corrected density value obtained by calculation is compared with predetermined standard density data in step a6. This standard density data is threshold data used to determine whether an irradiation dosage is proper or not. In step a7, the corrected density value calculated in the preceding step is judged whether it is larger than the standard density data or not. When the corrected density value is larger than the standard density data, the operation process is shifted to step a8, where a delay of predetermined time corresponding to the distance between the dosage sensor 6 and the CCD sensor 5 is given, and an instruction is delivered to the X-ray dosage control circuit 30 to decrease the irradiation dosage of the X-ray source 2. On the other hand, when the corrected density value is smaller than the standard density data in step a9, the operation process is shifted to step a10, where the delay of predetermined time corresponding to the distance between the dosage sensor 6 and the CCD sensor 5 is given, and an instruction is delivered to the X-ray dosage control circuit 30 to increase the irradiation dosage of the X-ray source 2. When the corrected density value obtained by calculation is nearly equal to the standard density data, the operation process passes step a11 without performing dosage correction. In this way, the output from the dosage sensor 6 is compared with the standard density data, and X-ray irradiation dosage is feedback-controlled depending on the result of the comparison, thereby affording a proper image density.

Next, whether tomographic imaging is completed or not is judged in step a12. When it is not completed, the imaging operation is shifted to the next imaging region in step a13. The rotation of the swivel member 4 and the TDI operation of the CCD sensor 5 continue, and steps a1 to a11 are repeated. When the imaging operation is completed, a high-quality tomographic image having few variations in density as a whole can be obtained.

Figure 6:
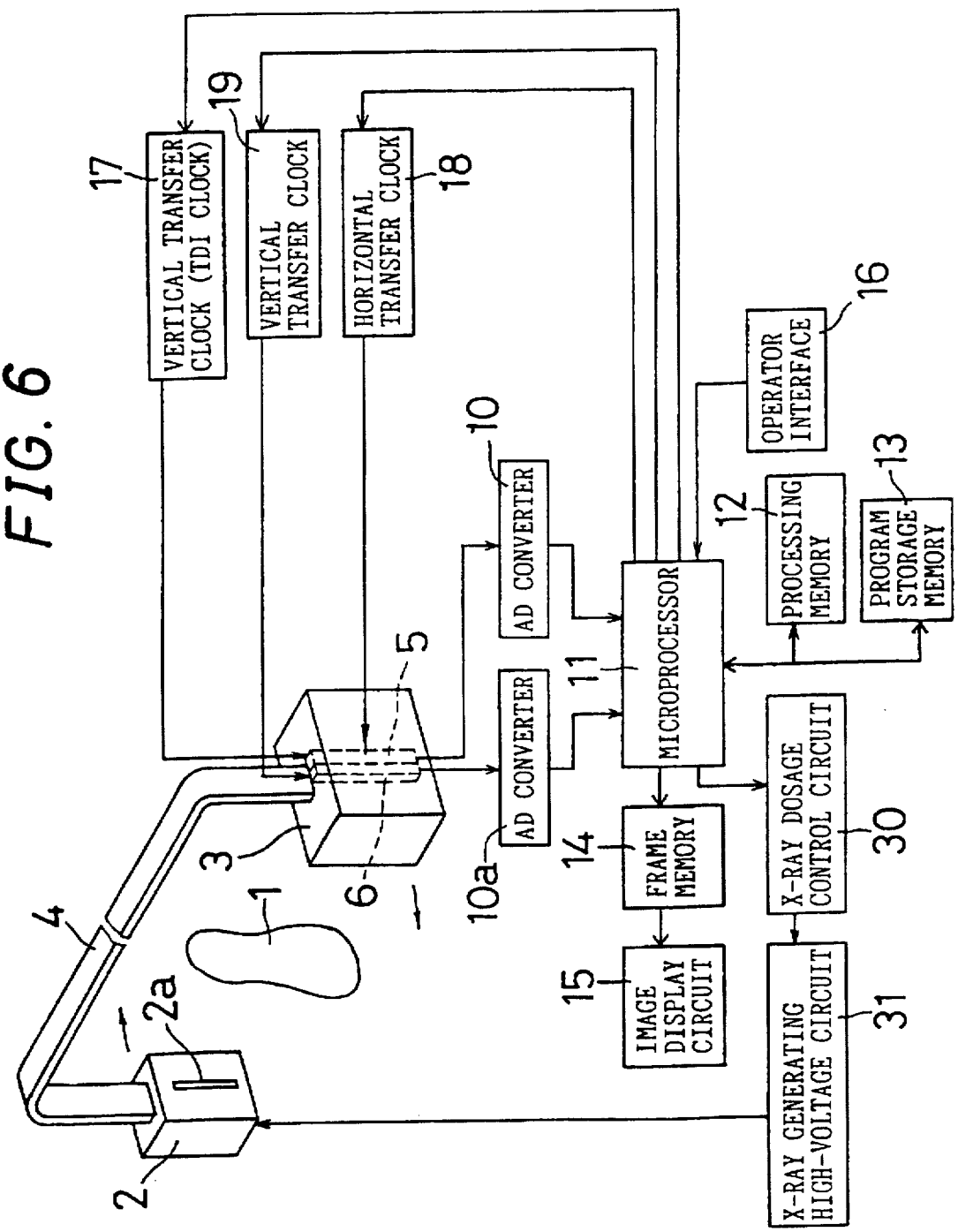
FIG. 6 is a view showing the construction of a third embodiment of the invention.

FIG. 6 is a view showing the construction of a third embodiment of the invention. The medical X-ray imaging apparatus in accordance with the third embodiment comprises an X-ray source 2 for emitting X-rays having a vertically long slit shape toward a subject 1, such as the human body, an X-ray imaging device 3 for detecting an image of X-rays having passed through the subject 1 and a swivel member (such as a rotary arm) for holding the X-ray source 2 and the X-ray imaging device 3 opposed to each other and for rotating the X-ray source 2 and the X-ray imaging device 3 around the subject 1. An X-ray tube (not shown) is provided in the X-ray source 2. The X-ray irradiation dosage to the subject 1 is controlled by adjusting imaging conditions, such as tube voltage, tube current and conducting period. The X-rays generated by the X-ray tube are converted into an X-ray beam having a vertically long slit shape as the X-rays pass through a primary slit 2a.

The X-ray imaging device 3 is provided with a secondary slit (not shown) for allowing the X-rays from the X-ray source 2 to pass through. Furthermore, the X-ray imaging device 3 is provided with a scintillator for converting an incoming X-ray image into a visible light image, a fiber optic plate (FOP) for guiding the visible light image from the scintillator and a CCD (charge-coupled device) sensor 5 for taking the visible light image from the fiber optic plate. The CCD sensor 5 has a plurality of light-receiving pixels arranged in two dimension and performs the TDI (time delay integration) operation, where the frequency of the charge transfer clock is changed depending on the rotation speed of the swivel member 4 so as to take an image of a predetermined tomographic face.

The swivel member 4 is supported so as to be rotatable in a horizontal plane around a position just above the subject 1. The rotation shaft of the swivel member 4 is driven by an arm motor, such as a stepping motor, and provided with an angle detector for detecting a change in rotation angle with time. The output of the angle detector is used to synchronize the TDI operation with the charge transfer clock signal.

The X-ray imaging device 3 is provided with a dosage sensor 6 for detecting an X-ray dosage having passed the subject 1. The dosage sensor 6 is provided adjacent to the CCD sensor 5 forward in the rotation direction of the CCD sensor 5 so as to detect the X-ray dosage in advance to be imaged at the CCD sensor 5. The dosage sensor 6 of this embodiment has the same structure as that of the CCD sensor 5, where a plurality of light-receiving pixels are arranged in two dimensions.

The image signal outputted from the CCD sensor 5 is converted into 8-bit (=256 levels) digital data, for example, by an AD converter 10 and supplied to a microprocessor 11 and then stored in a frame memory 14. The image data stored in the frame memory 14 is subjected to a predetermined imaging processing, and indicated by an image display circuit 15, such as a CRT (cathode ray tube), so as to be used for a variety of medical diagnostic purposes. In addition, a processing memory 12 required for signal processing, a program storage memory 13 and an operator interface 16, such as a keyboard and panel switches, are connected to the microprocessor 11.

The microprocessor 11 outputs vertical transfer clock 17, 19 so that the charges received and stored by the CCD sensor 5 and the dosage sensor 6 can be transferred in the rotation direction of the swivel member 4. The microprocessor 11 also outputs a horizontal transfer clock 18 so that a single scanning line of charges vertically transferred in the CCD sensor 5 and the dosage sensor 6 can be read.

On the other hand, an analog signal proportional to the dosage having passed through the subject 1 is outputted from the dosage sensor 6 provided adjacent to the CCD sensor 5. The signal is converted into 8-bit (=256 levels) digital data, for example, by an AD converter 10a, supplied to a microprocessor 11 and stored in a processing memory 12 so as to be used for feedback control of X-rays generated from the X-ray source 2.

In accordance with instructions from the microprocessor 11, an X-ray dosage control circuit 30 controls an X-ray generating high-voltage circuit 31 and feedback-controls the X-ray tube of the X-ray source 2 to adjust imaging conditions, such as tube voltage, tube current, conducting period, etc.

Figure 7:
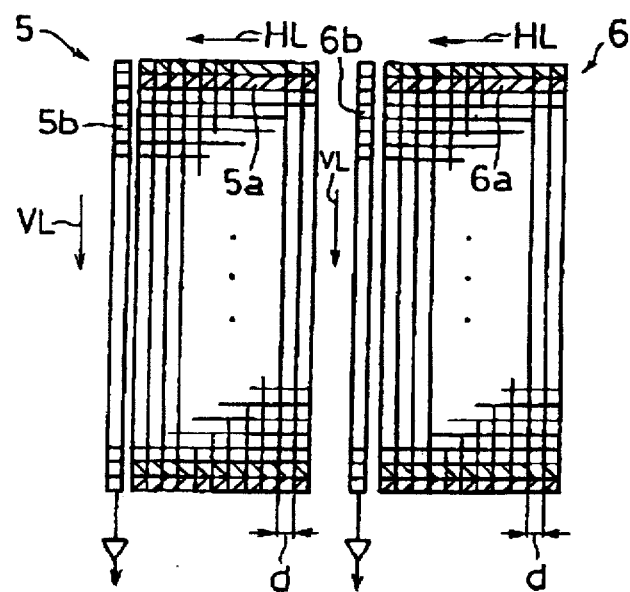
FIG 7 is a view showing the arrangement of the CCD sensor 5 and the dosage sensor 6.

FIG. 7 is a view showing the arrangement of the CCD sensor 5 and the dosage sensor 6. The dosage sensor 6 of this embodiment has the same structure as that of the CCD sensor 5 and provided adjacent to the CCD sensor 5 forward in the rotation direction of the CCD sensor 5. As described in FIG. 3, in the CCD sensor 5 and the dosage sensor 6, a vertically long light-receiving portion is formed by a plurality of light-receiving pixels arranged in a two-dimensional matrix. Each light-receiving pixel is electrically connected to a plurality of vertical shift registers 5a, 6a (shaded by slant lines in FIG. 7) arranged in horizontal direction HL. The output from each of the vertical shift registers 5a, 6a is transferred sequentially in horizontal direction HL by the vertical transfer clock. The output portions of the vertical shift registers 5a, 6a are electrically connected to the horizontal shift registers 5b, 6b arranged in vertical direction VL, respectively. Each time the vertical shift registers 5a, 6a complete the transfer of a charge for one pixel, all the charges are transferred outward. In this way, the X-ray image is converted into a time series electrical signal by the combination of horizontal scanning and vertical scanning. Although the CCD sensor 5 and the dosage sensor 6 shown in FIG. 7 are of a full-frame transfer (FFT) type with no charge storage portion, a frame transfer (FT) type with charge storage portions as many as the light-receiving pixels may also be applicable.

Figure 8:
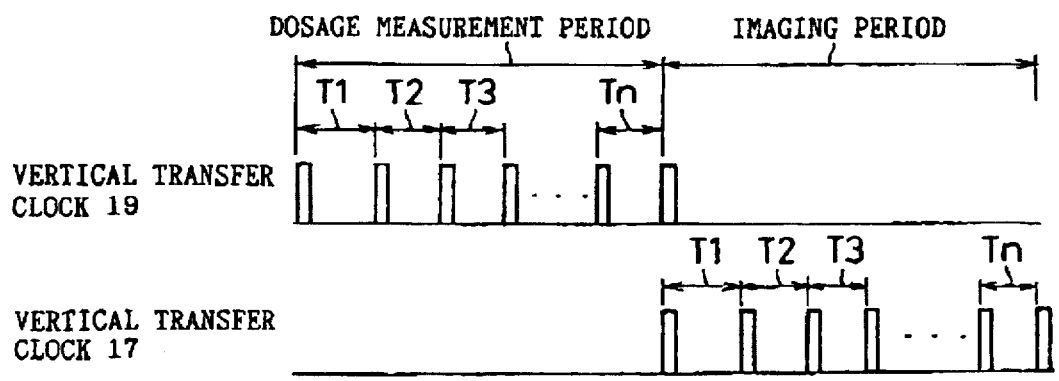
FIG. 8 is a timing chart of vertical transfer clocks 17, 19.

FIG. 8 is a timing chart showing the vertical transfer clocks 17, 19. Pulse intervals T1, T2, ..., Tn of the vertical transfer clocks 17, 19 is changed slightly because of the TDI operation. As a whole, the vertical transfer clock 17 for driving the CCD sensor 5 is delayed behind the vertical transfer clock 19 for driving the dosage sensor 6 by the time corresponding to the distance between the dosage sensor 6 and the CCD sensor 5. Therefore, dosage detection is performed earlier by the dosage sensor 6 than by the CCD sensor 6.

Figure 9:
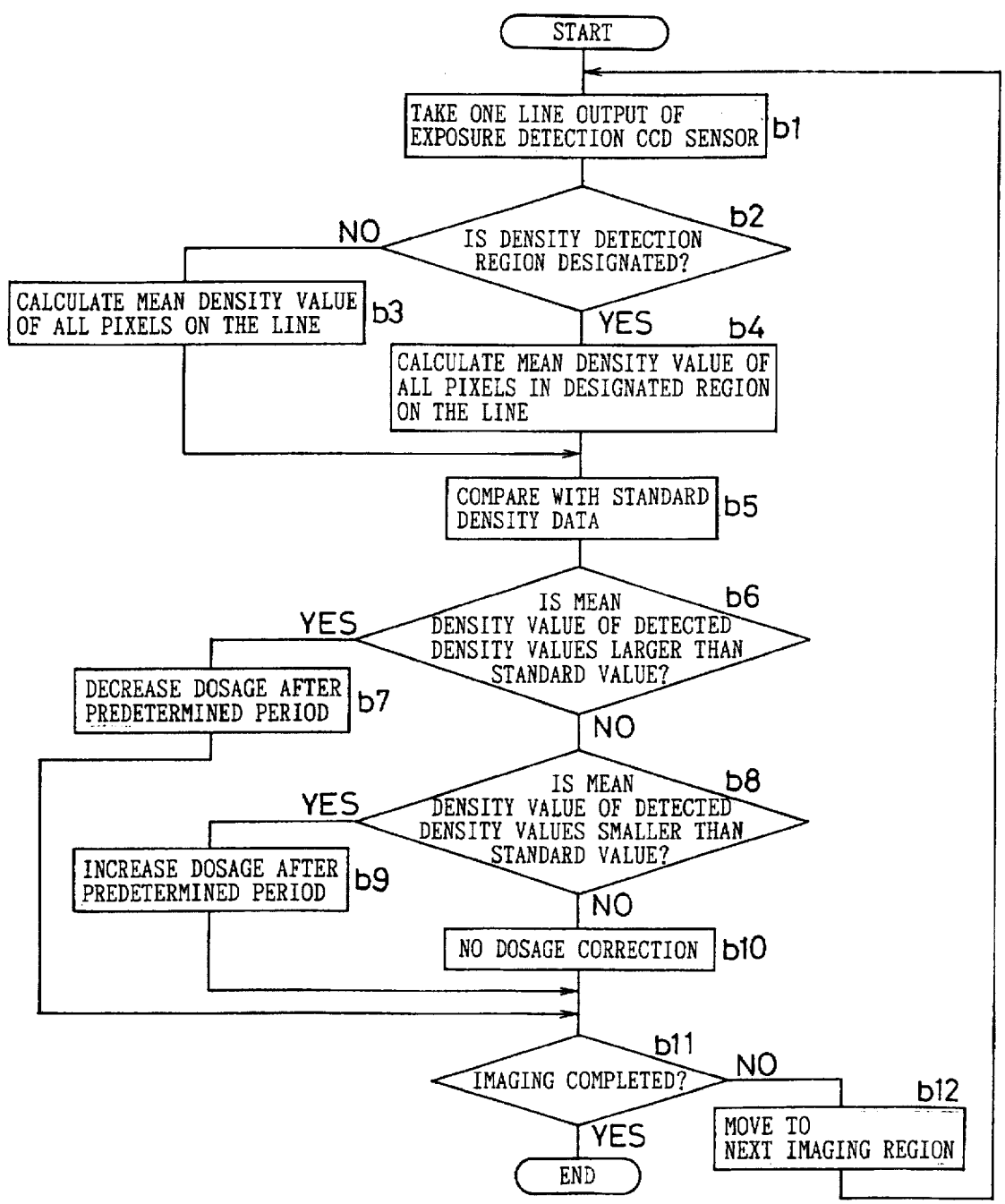
FIG. 9 is a flowchart showing the operation of the third embodiment.

FIG. 9 is a flowchart showing the operation of the third embodiment. When tomographic imaging starts, a single line of output from the CCD sensor constituting the dosage sensor 6 is supplied to the microprocessor 11 in step b1. Next, whether a density detection region has been designated or not is determined in step b2. When no region has been designated, the mean value of the density in all the regions is calculated in step b3. On the other hand, when an region has been designated, the mean value of the density of all the pixels in the designated region on a single line is calculated in step b4.

Next, the mean density value calculated in the preceding step is compared with predetermined standard density data in step b5. This standard density data is threshold data used to judge whether an irradiation dosage is proper or not. In step b6, the mean density value is judged whether it is larger than the standard density data or not. When the mean density value is larger than the standard density data, the operation process is shifted to step b7, where a delay of predetermined time corresponding to the distance between the dosage sensor 6 and the CCD sensor 5 is given, and an instruction is delivered to the X-ray dosage control circuit 30 to decrease the irradiation dosage of the X-ray source 2. On the other hand, when the mean density value is smaller than the standard density data in step b8, the operation process is shifted to step b9, where a delay of predetermined time corresponding to the distance between the dosage sensor 6 and the CCD sensor 5 is given, and an instruction is delivered to the X-ray dosage control circuit 30 to increase the irradiation dosage of the X-ray source 2. When the corrected density value obtained by calculation is nearly equal to the standard density data, the operation process passes step b10 without performing dosage correction. In this way, the output from the dosage sensor 6 is compared with the standard density data, and X-ray irradiation dosage is feedback-controlled depending on the result of the comparison to obtain a proper image density.

Next, whether tomographic imaging is completed or not is judged in step b11. When it is not completed, the imaging operation is shifted to the next imaging region in step b12. The rotation of the swivel member 4 and the TDI operation of the CCD sensor 5 and the dosage sensor 6 continue, and steps b1 to b10 are repeated. When the imaging operation is completed, a high-quality tomographic image having few variations in density as a whole can be obtained.

Figure 10:
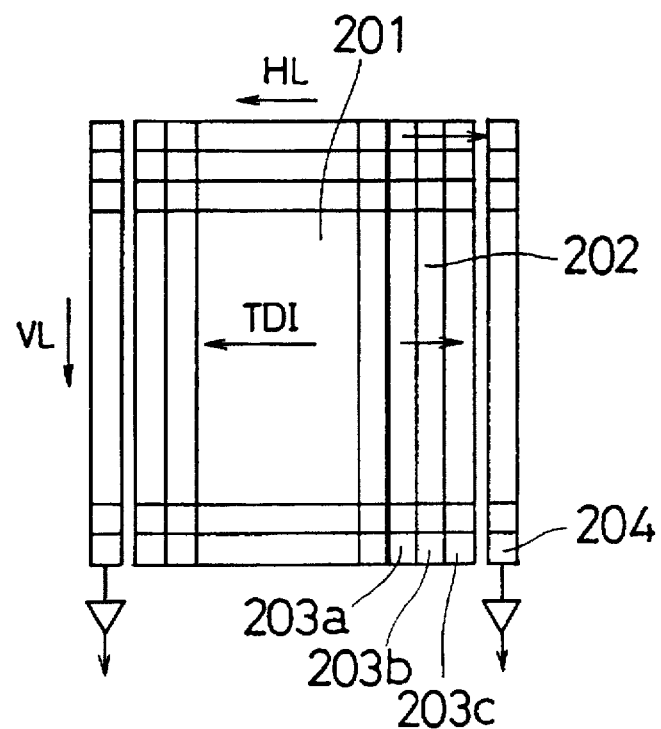
FIG. 10 is a view showing another embodiment of a planar arrangement of the CCD sensor and the dosage sensor.

FIG. 10 is a view showing another planar arrangement of the CCD sensor and the dosage sensor. Each effective pixel of a CCD sensor 201 is composed of a plurality of vertical shift registers arranged in horizontal direction HL, a horizontal shift register disposed in vertical direction VL and an amplifier for delivering signal charges, just as the above-mentioned embodiment. A dosage sensor 202 comprises CCD pixels having a size identical to or different from that of the effective pixels of the CCD sensor 201 and disposed adjacent to the effective pixels of the CCD sensor 201. Furthermore, the dosage sensor 202 has a structure symmetrical to that of the CCD sensor 201. With this structure, the number of the CCD pixels constituting the dosage sensor is set to be less than the number of the pixels arranged in horizontal direction HL of the CCD sensor 201.

As with the above-mentioned embodiment, the CCD sensor is structured so as to take an image of a predetermined tomographic surface by performing the TDI operation, where the frequency of the charge transfer clock is changed depending on the rotation speed of the swivel member. On the other hand, the CCD constituting the dosage sensor is structured so as to transfer charges in the direction opposite to the direction of signal charge integration performed in the TDI operation. Each CCD pixel is disposed closest to the TDI start position. Furthermore, the signal at the CCD pixels constituting the dosage sensor is added to the horizontal shift register of the sensor in a single clock cycle of the TDI operation of the CCD sensor 201. CCD202 constituting the dosage sensor comprises three pixels: 203a, 203b and 203c, for example. Its horizontal shift register is designated by numeral 204. In a single clock cycle of the TDI operation, the signals at pixels: 203a, 208b and 203c are added to the register 204. As a result, a signal train can be outputted from the dosage sensor depending on the signal train of the CCD sensor. With this method, by using the signal train from the dosage sensor 202, the X-ray dosage delivered from the CCD sensor 201 at a time before the duration necessary for the TDI operation can be monitored. X-ray control can thus be attained by using the structure shown in FIG. 1.

Figure 11:
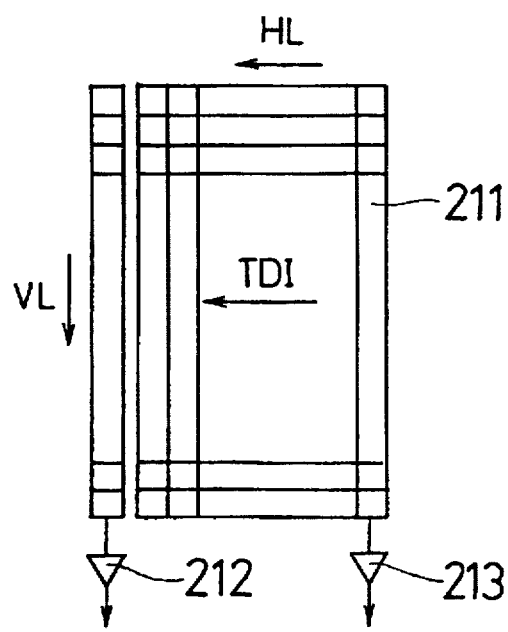
FIG. 11 is a view showing still another embodiment of a planar arrangement of the CCD sensor and the dosage sensor.

FIG. 11 is a view showing still another plane arrangement of the CCD sensor and the dosage sensor. Each effective pixel of the CCD sensor is composed of a plurality of vertical shift registers arranged in horizontal direction HL, a horizontal shift register disposed in vertical direction VL and an amplifier for outputting signal charges, as in the above-mentioned embodiment. On the other hand, the dosage sensor comprises a CCD pixel array 211 disposed at the start position of the TDI operation of the CCD sensor in the same direction as vertical direction VL and a nondestructive signal detector, that is, a floating gate amplifier 213 connected to all the pixels of the CCD pixel array 211. It is generally known that the floating gate amplifier 213 can detect signals without destructing signal charges, unlike a floating diffusion amplifier 212 which destruct signal charges at the time of reading signal charges.

With the invention, the nondestructive signal detector 213 is disposed at the start position of the TDI operation as a dosage sensor, independently of the signal detector 212 for detecting signals from the CCD sensor. Therefore, since the X-ray dosage delivered from the CCD sensor at a time before the duration necessary for the TDI operation can be monitored, X-ray control can be attained by using the structure shown in FIG. 1.

In the embodiments shown in FIGS. 10 and 11, since the dosage sensor can be disposed integral with and adjacent to the substrate of the X-ray imaging CCD sensor, the sensors can be made compact and assembled easily, which is advantageous in that the sensors can be manufactured at low cost.

The invention may be embodied in other specific forms without departing from the spirit or essential characteristics thereof. The present embodiments are therefore to be considered in all respects as illustrative and not restrictive, the scope of the invention being indicated by the appended claims rather than by the foregoing description and all changes which come within the meaning and the range of equivalency of the claims are therefore intended to be embraced therein.

What is claimed is:

1. A medical X-ray imaging apparatus comprising:
   an X-ray generator for emitting X-rays toward a subject;
   an X-ray imaging device for detecting an image of X-rays having passed through the subject;
   a swivel member for rotating the X-ray generator and the X-ray imaging device that are opposed to each other around the subject; and
   display means for displaying an image signal from the X-ray imaging device,
   wherein the X-ray imaging device includes a CCD sensor having a plurality of light-receiving pixels arranged in two dimensions and the frequency of a charge transfer clock is changed depending on the rotation speed of the swivel member to perform imaging of a predetermined tomographic plane, and the X-ray imaging device further includes a dosage sensor for detecting an X-ray dosage having passed the subject, and the dosage sensor is provided adjacent to the CCD sensor forward in the rotation direction of the CCD sensor to perform feedback-control of the X-ray dosage emitted by the X-ray generator.

2. The medical X-ray imaging apparatus according to claim 1, wherein the dosage sensor has a single or plural light-receiving surfaces.

3. The medical X-ray imaging apparatus according to claim 1, wherein the dosage sensor has the same structure as the structure of the CCD sensor.

4. The medical X-ray imaging apparatus according to claim 1, wherein the X-ray dosage from the X-ray generator is feedback-controlled on the basis of the ratio of the output from the dosage sensor to the frequency of the charge transfer clock.

5. The medical X-ray imaging apparatus according to claim 1, wherein the dosage sensor comprise a CCD sensor disposed adjacent to said CCD sensor and configured so as to be capable of transferring charges in the direction opposite to the CCD sensor.

6. The medical X-ray imaging apparatus according to claim 1, wherein the dosage sensor comprises a nondestructive signal detector composed of a floating gate amplifier disposed at an array of CCD pixels provided adjacent to said CCD sensor.

* * * * *